(12) United States Patent
Sologub

(10) Patent No.: US 12,318,575 B2
(45) Date of Patent: Jun. 3, 2025

(54) MULTIPURPOSE CAPACITIVE SENSOR FOR FLUID PUMPS

(71) Applicant: CareFusion 303, Inc., San Diego, CA (US)

(72) Inventor: Vadym Sologub, Limerick (IE)

(73) Assignee: CareFusion 303, Inc., San Diego, CA (US)

( * ) Notice: Subject to any disclaimer, the term of this patent is extended or adjusted under 35 U.S.C. 154(b) by 1157 days.

(21) Appl. No.: 17/167,805

(22) Filed: Feb. 4, 2021

(65) Prior Publication Data
US 2021/0244879 A1    Aug. 12, 2021

Related U.S. Application Data

(60) Provisional application No. 62/975,422, filed on Feb. 12, 2020.

(51) Int. Cl.
*A61M 5/168*    (2006.01)
*A61M 5/36*    (2006.01)

(52) U.S. Cl.
CPC ........ *A61M 5/16831* (2013.01); *A61M 5/365* (2013.01); *A61M 2205/18* (2013.01); *A61M 2205/3317* (2013.01); *A61M 2205/52* (2013.01); *A61M 2205/581* (2013.01); *A61M 2205/587* (2013.01)

(58) Field of Classification Search
CPC .............. A61M 5/16831; A61M 5/365; A61M 2205/18; A61M 2205/3317; A61M 2205/52; A61M 2205/581; A61M 2205/587
See application file for complete search history.

(56) References Cited

U.S. PATENT DOCUMENTS

| | | |
|---|---|---|
| 4,382,753 A | 5/1983 | Archibald |
| 6,280,408 B1 | 8/2001 | Sipin |
| | (Continued) | |

OTHER PUBLICATIONS

Ahmed, M. (2009). "Capacitive Air Bubble Detector Operated at Different Frequencies for Application in Hemodialysis." World Academy of Science, Engineering and Technology, Open Science Index 26, International Journal of Electrical and Computer Engineering, 3(2), 158-161.

(Continued)

*Primary Examiner* — Lauren P Farrar
(74) *Attorney, Agent, or Firm* — Mintz Levin Cohn Ferris Glovsky and Popeo, P.C.

(57) ABSTRACT

A method may include measuring a first side capacitance value from a first side capacitor of an infusion pump, measuring a second side capacitance value from a second side capacitor of the infusion pump, and measuring a central capacitance value from a central capacitor of the infusion pump. The method may include determining a total side capacitance value by totaling the first side capacitance value and the second side capacitance value. The method may also include comparing the total side capacitance value with the central capacitance value. The method may also include detecting the presence of air within a fluid delivery tube coupled to the infusion pump when the central capacitance value is different from the total side capacitance value. Related methods and articles of manufacture, including apparatuses and computer program products, are also disclosed.

16 Claims, 10 Drawing Sheets

(56) References Cited

U.S. PATENT DOCUMENTS

| | | | |
|---|---|---|---|
| 2006/0025725 A1* | 2/2006 | Cassidy | A61M 5/36 604/123 |
| 2009/0075129 A1* | 3/2009 | Sparks | G01F 1/849 73/19.03 |
| 2009/0319204 A1 | 12/2009 | Brown | |
| 2014/0142537 A1* | 5/2014 | Gibson | A61M 5/14546 604/67 |

OTHER PUBLICATIONS

Caesarea Medical Electronics. CME—BodyGuard 323. https://www.cme-infusion.com/bodyguard-323, 2 pages, accessed May 1, 2021.

* cited by examiner

MULTIPURPOSE CAPACITIVE SENSOR FOR FLUID PUMPS

CROSS-REFERENCE TO RELATED APPLICATIONS

The present application claims priority to U.S. Provisional Application No. 62/975,422, filed on Feb. 12, 2020, and entitled "Multipurpose Capacitive Sensor for Fluid Pumps," the entirety of which is incorporated by reference herein.

TECHNICAL FIELD

The subject matter described herein relates generally to the dispensation of fluids and more specifically to a pump system for an infusion device for the delivery of fluid medications.

BACKGROUND

Fluid pumps, such as infusion pumps, administer therapy to patients by delivering a medication or other fluid to the patient. These pumps may include a compartment for an infusion set, with a door providing access to and securing the compartment. The infusion set may include a fluid delivery tube, such as intravenous tubing or other administration sets. During use of the pumps, air may become trapped in the fluid delivery tube of the infusion set, which if left unmonitored, may result in a high risk of air entering the patient's bloodstream, thereby causing an air embolism or other medical complications. Air present within the fluid delivery tube may be difficult to detect. Sensors and detection methods may generally be unreliable, difficult to assemble, expensive, and require a significant amount of device resources (e.g., power, processing time, memory, network bandwidth, and the like).

SUMMARY

Systems, methods, and articles of manufacture, including computer program products, are provided for detecting the presence of air within a fluid delivery tube of a fluid pump such as an infusion pump.

According to some aspects, an infusion pump system may detect a presence of air within a fluid delivery tube coupled to an infusion pump for delivery of a medication to a patient. The infusion pump system may include a door, a base, and a capacitor system. The door may include a first side portion, a second side portion, and a central portion positioned between the first side portion and the second side portion. The base may include a first side electrode, a second side electrode, and a central electrode positioned between the first side electrode and the second side electrode. The fluid delivery tube may be positioned between the central electrode and the central portion of the door. The capacitor system may include a first side capacitor formed by the first side electrode and the first side portion, a second side capacitor formed by the second side electrode and the second side portion, and a central capacitor formed by the central portion, the fluid delivery tube, and the central electrode. The presence of air within the fluid delivery tube may be detected when a total side capacitance value is different from a central capacitance value of the central capacitor. The total side capacitance value may be a total of a first side capacitance value of the first side capacitor and a second side capacitance value of the second side capacitor.

In some aspects, the presence of air within the fluid delivery tube is detected when the central capacitance value is less than the total capacitance value. In some aspects, the door comprises a metallic material. In some aspects, the base comprises a substrate, and the first side electrode, the second side electrode, and the central electrode are etched into the substrate. In some aspects, the substrate is a printed circuit board.

In some aspects, the door is parallel to the base. In some aspects, a side distance between the first side electrode and the first side portion of the door is less than a central distance between the central electrode and the central portion of the door. In some aspects, the infusion pump system includes the fluid delivery tube and the infusion pump.

According to some aspects, a method is provided. The method may include measuring a first side capacitance value from a first side capacitor of an infusion pump. The first side capacitor may be formed by a first side portion of a door of the infusion pump and a first side electrode of the infusion pump. The method may also include measuring a second side capacitance value from a second side capacitor of the infusion pump. The second side capacitor may be formed by a second side portion of the door and a second side electrode of the infusion pump. The method may also include determining a total side capacitance value by totaling the first side capacitance value and the second side capacitance value. The method may also include measuring a central capacitance value from a central capacitor of the infusion pump. The central capacitor may be formed by a central portion of the door, a central electrode of the infusion pump, and a fluid delivery tube coupled to the infusion pump for delivering a medication to a patient. The method may also include comparing the total side capacitance value to the central capacitance value. The method may also include detecting the presence of air within the fluid delivery tube when the central capacitance value is different from the total side capacitance value. The method may also include indicating to the patient that air is present within the fluid delivery tube and/or stopping flow of the medication within the fluid delivery tube upon detecting the presence of air within the fluid delivery tube.

In some aspects, the method also includes determining that the central capacitance value is less than the total side capacitance value. The method may also include detecting the presence of air within the fluid delivery tube based on the determination that the total side capacitance value is less than the central capacitance value.

In some aspects, the indicating comprises one or more of playing a sound and flashing a light via a display of the infusion pump.

In some aspects, the detecting the presence of air further includes: determining a volume of the air that is present within the fluid delivery tube based on the central capacitance value. In some aspects, the detecting the presence of air further includes determining that the volume of the air is greater than or equal to a threshold volume of air. In some aspects, the detecting the presence of air further includes determining a volume of a first air bubble of the air within the fluid delivery tube based on the central capacitance value. In some aspects, the detecting the presence of air further includes determining that the volume of the first air bubble is greater than or equal to a threshold volume of air, and indicating to the patient that air is present within the fluid delivery tube and/or stopping flow of the medication within the fluid delivery tube upon determining that the volume of the first air bubble is greater than or equal to the threshold volume of air.

In some aspects, the detecting the presence of air further includes determining that the volume of the first air bubble is less than a threshold volume of air, determining a second volume of a second air bubble of the air within the fluid delivery tube based on a second central capacitance value, determining a total volume of air within the fluid delivery tube by totaling the volume of the first air bubble and the second volume of the second air bubble, and indicating to the patient that air is present within the fluid delivery tube and/or stopping flow of the medication within the fluid delivery tube upon determining that the total volume is greater than or equal to the threshold volume of air.

Implementations of the current subject matter can include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to a pump system for detecting the presence of air in a fluid delivery tube of an infusion pump, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
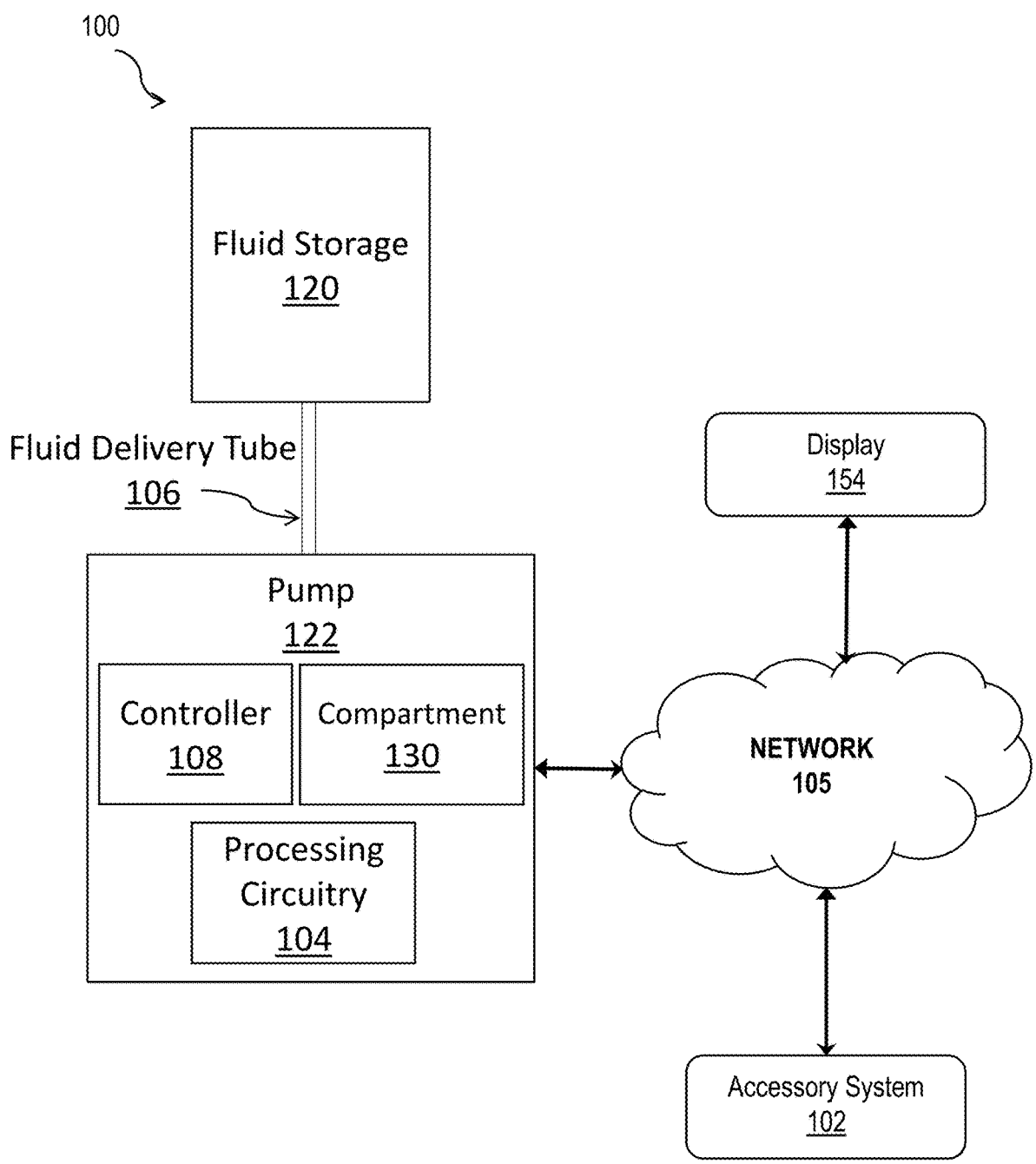
FIG. 1 depicts a system diagram illustrating a pump system, in accordance with some example embodiments.

Pumps, such as infusion pumps, administer therapy to patients by delivering a medication or other fluid to the patient. These pumps may include a compartment for an infusion set, with a door providing access to and securing the compartment. The infusion set may include a fluid delivery tube, such as intravenous (IV) tubing or other administration sets. During use of the pumps, air may become trapped in the fluid delivery tube of the infusion set, which if left unmonitored, may result in a high risk of air entering the patient's bloodstream, thereby causing an air embolism or other medical complications. Air present within the fluid delivery tube may be difficult to detect and detection methods may generally be unreliable, difficult to assemble, expensive, and require a significant amount of power. The pump system described herein may reliably detect the presence of air in delivered medication (or other fluid) by the pump, simplify the assembly of the pump system, and reduce resource requirements of the pump system.

For example, the pump system may include three capacitors (or capacitive sensors and/or the like), each defined by an electrode positioned on and/or within the compartment, and at least a portion of the door of the compartment, which may be made of metal and/or another conductive material. The capacitors may include one, two, three, four, five or more capacitors. For example, the capacitors may include a central capacitor and two side capacitors positioned on opposing sides of the central capacitor. The fluid delivery tube may be positioned within the central capacitor (e.g., between the electrode and door), while there may be no or minimal space (e.g., less than 10 mm, 5 mm, 3 mm, 1 mm, and/or the like) between the electrode and the door of the two side capacitors. Thus, the fluid delivery tube may define a dielectric material of the central capacitor.

The pump system may detect the presence of air within the fluid delivery tube when the capacitance of the central capacitor does not match and/or is not within a range of a total capacitance of the two side capacitors. For example, capacitance may be determined at least in part based on the dielectric constant of the material positioned within each capacitor. As a result, when air enters the fluid delivery tube, the dielectric constant of the material (e.g., the fluid medication) positioned within the central capacitor changes, thereby causing the capacitance of the central capacitor to change, while the capacitance of the two side capacitors remains constant. Comparing the total capacitance of the two side capacitors to the capacitance of the central capacitor allows for reliable in-line detection of air, by the pump system. Based on the measured capacitances of the central and side capacitors, the pump system described herein may additionally and/or alternatively detect whether the infusion set is present in the infusion pump, measure whether the door of the infusion pump is properly closed during use, and/or detect when a different type of medication is injected into the infusion set.

Some examples of infusion pumps may employ a pair of ultrasonic elements or sensors (e.g., transducers), including an emitter and a receiver. The emitter may emit ultrasonic signals and the receiver may receive the ultrasonic signals. The emitter and receiver may be expensive, unreliable, and require significant driving power. For example, as noted above, infusion pumps may include a compartment for an infusion set, with a door providing access to and securing the compartment. The emitter and receiver may be coupled to various portions of an infusion set. As an example, the emitter may be attached to the door, and the receiver may be attached elsewhere on the infusion set and/or within the compartment, or vice versa. Mounting one of these components on the door, with the other being mounted to the compartment may be unreliable since wires connecting these components, or with external components, may bend when the door is opened and closed, and may be expensive to replace, especially in wearable devices. Moreover, because at least one of the components is moving, the material of the moving component (e.g., ceramic) vibrates in use, causing cracks in the component, and allowing moisture to enter the component. This may be especially problematic in non-hospital environments, where there may be more movement of the device, and inconsistency in the use of the device. The pump system described herein may reliably detect the presence of air, by, for example, providing a redundancy in the capacitance measurements. The pump system described herein may additionally and/or alternatively consume minimal power and simplify the assembly of the pump system. For example, the pump system described herein may be integrally formed or at least partially integrally formed with the compartment of the pump (e.g., with the door), thereby simplifying the assembly of the pump system and reducing the likelihood of mechanical failure of the pump system.

Some examples of infusion pumps may alternatively include optical sensors to detect whether air is present in the fluid delivery tube of an infusion set. However, optical sensors may only be feasible in limited circumstances, such as when the fluid passing through the fluid delivery tube is transparent. Use of optical sensors may also require a significant amount of power to drive an optimal emitter communicating with the sensors. The pump system described herein may be used with any type of fluid passing through the fluid delivery tube, as the pump system measures capacitance based on the dielectric constant of the fluid within the fluid delivery tube. The pump system may also consume a minimal amount of power.

Other examples of infusion pumps may include a single capacitor, which may be very large, to detect whether air is present in the fluid delivery tube of an infusion set. However, using only a single capacitor may result in unreliable measurements, as the measurements would be susceptible to environmental changes, such as changes in temperature, humidity, and air pressure. The pump system described herein compares two capacitance measurements (e.g., a capacitance of the central capacitor, and a total capacitance of the two side capacitors), which increases the reliability and stability of the pump system. The pump system described herein may also include relatively small capacitors, which may be capable of measuring small changes in capacitance, such as in the range of pico-farads.

FIG. 1 depicts a system diagram illustrating a pump system 100, in accordance with some example embodiments. Referring to FIG. 1, the pump system 100 may include a fluid storage 120, a pump (also referred to herein as an "infusion device") 122, a fluid delivery tube 106 connecting the fluid storage 120 and the pump 122, a network 105, an accessory system 102, and a display 154. In some example embodiments, the display 154 and/or the accessory system 102 may form a portion of the pump 122 and/or may be positioned within a housing of the pump 122.

The display 154 may form a part of the pump 122 or may be separately coupled as part of a client device. The display 154 may also include a user interface. The user interface may form a part of a display screen of the display 154 that presents information to the user and/or the user interface may be separate from the display screen. For example, the user interface may be one or more buttons, or portions of the display screen that is configured to receive an entry from the user. The client device may be a mobile device such as, for example, a smartphone, a tablet computer, a wearable apparatus, and/or the like. However, it should be appreciated that the client device may be any processor-based device including, for example, a desktop computer, a laptop computer, a workstation, and/or the like. Via the display 154, the user may be able to configure certain parameters of the pump 122, such as an air in line threshold, a rate limit, an alarm limit, and the like. Additionally, in some examples, via the display 154, the user may configure various drug protocols with default settings and safety parameters (e.g., setting a limit to a dose of a drug).

The accessory system 102 may include an alarm, light (e.g., an LED), a sound source, and/or other indicator. The indicator may indicate to the user of one or more measurements, thresholds, or other detected events relating to the pump 122. For example, the indicator may indicate to the user that air is present in the fluid delivery tube 106. As noted above, the accessory system 102 may form a part of the pump 122 and/or the display 154, or may be separately coupled to the pump 122, such as via the network 105.

As FIG. 1 shows, the pump 122, the display 154, and/or the accessory system 102 may be communicatively coupled via a network 105. The network 105 may be any wired and/or wireless network including, for example, a public land mobile network (PLMN), a local area network (LAN), a virtual local area network (VLAN), a wide area network (WAN), the Internet, and/or the like.

The pump 122 may be any type of pump configured to move a fluid from a fluid storage 120, such as a reservoir, drip chamber, syringe, and/or the like, through a conduit or other tube, such as fluid delivery tube 106, to a destination (not shown) such as, for example, a patient. The pump 122 may be a syringe pump, an anesthesia delivery pump, infusion pump and/or a patient-controlled analgesic (PCA) pump configured to deliver a medication to a patient. However, it should be appreciated that the pump 122 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like. Additionally and/or alternatively, the pump 122 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like. Moreover, the pump 122 may be part of a patient care system that includes one or more additional pumps.

The pump 122 may include a compartment 130, a controller 108, and processing circuitry 104. As described in more detail below, the compartment 130 may include one or more capacitors, the processing circuitry 104 may process the capacitance measured by the one or more capacitors, and the controller 108 may control the processing circuitry 104 and/or may communicate with one or more other systems, such as the accessory system 102 and the display 154.

Figure 2:
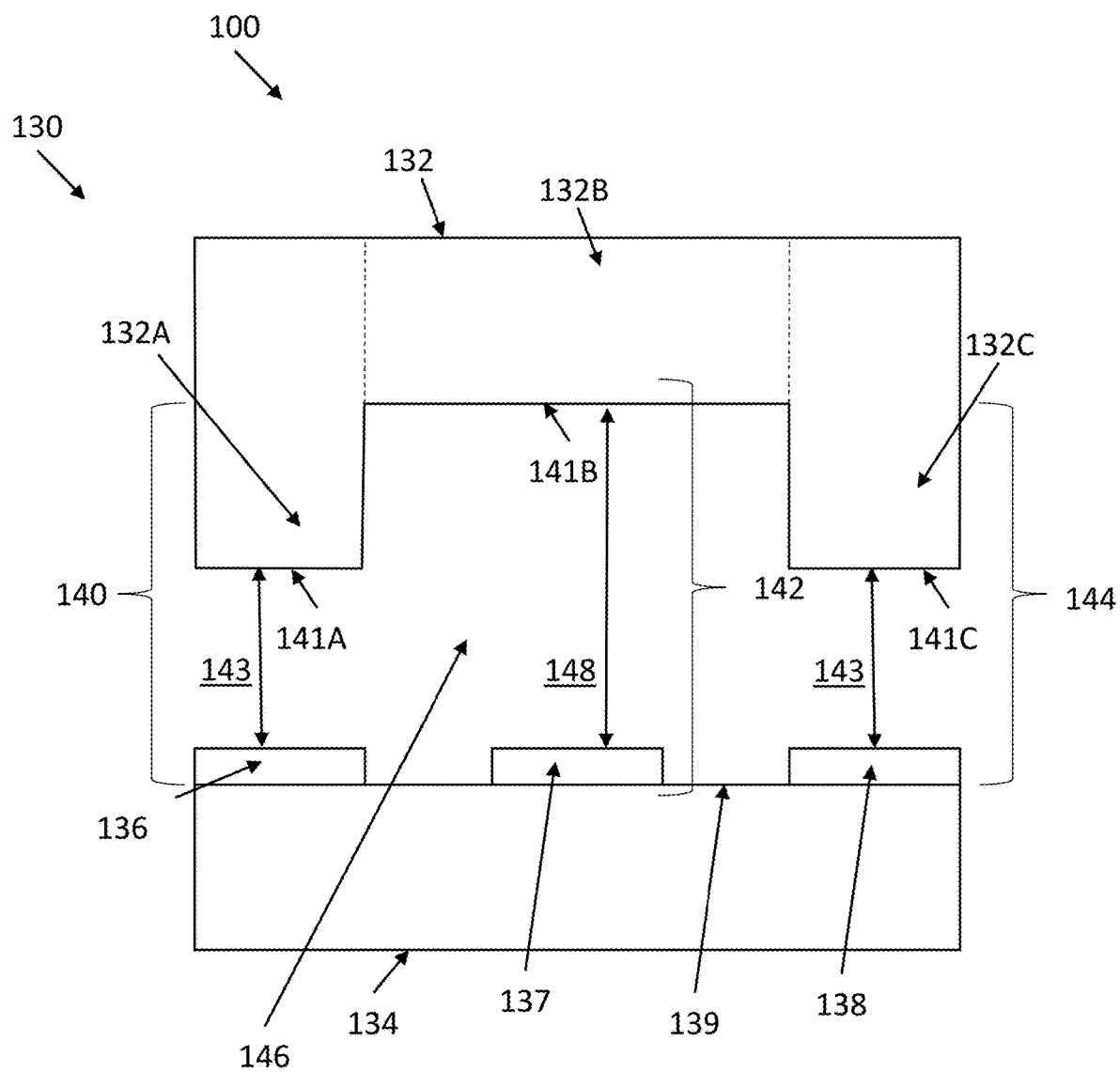
FIG. 2 schematically depicts an example compartment of a pump, in accordance with some example embodiments.
Figure 3A:
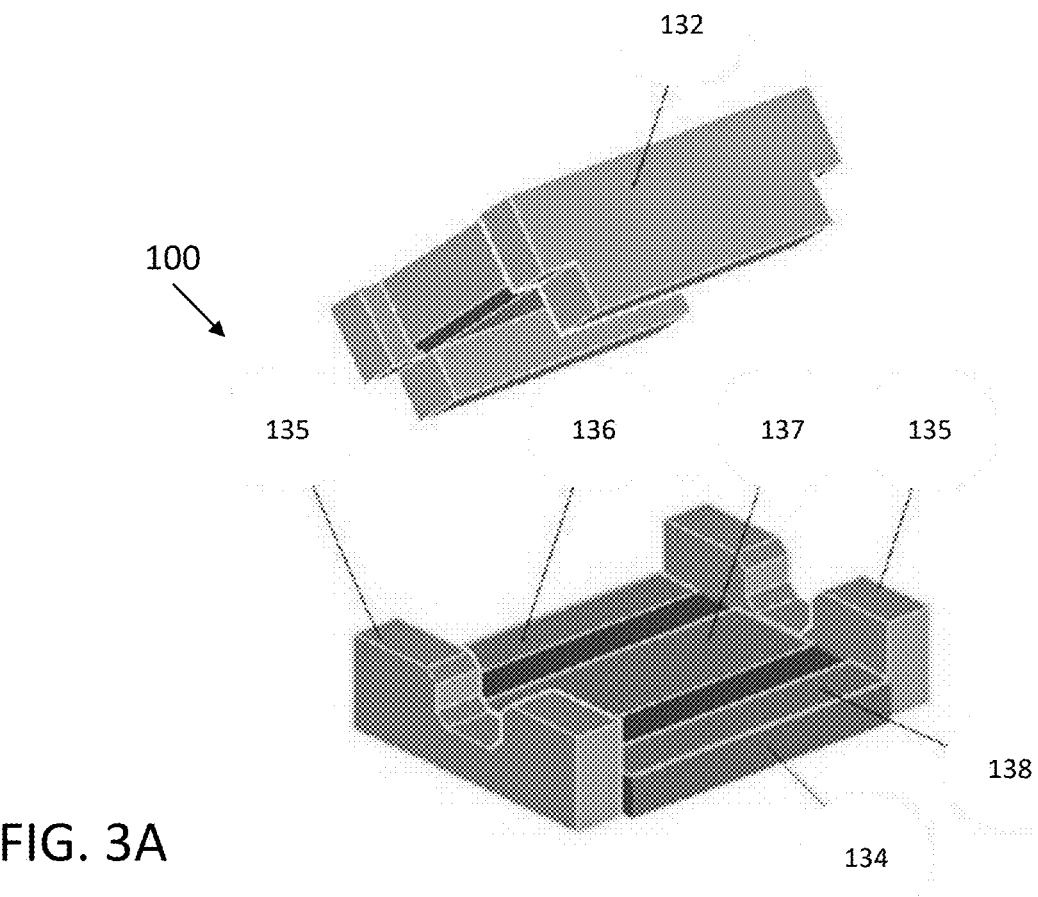
FIG. 3A depicts another example compartment of a pump, in accordance with some example embodiments.
Figure 3B:
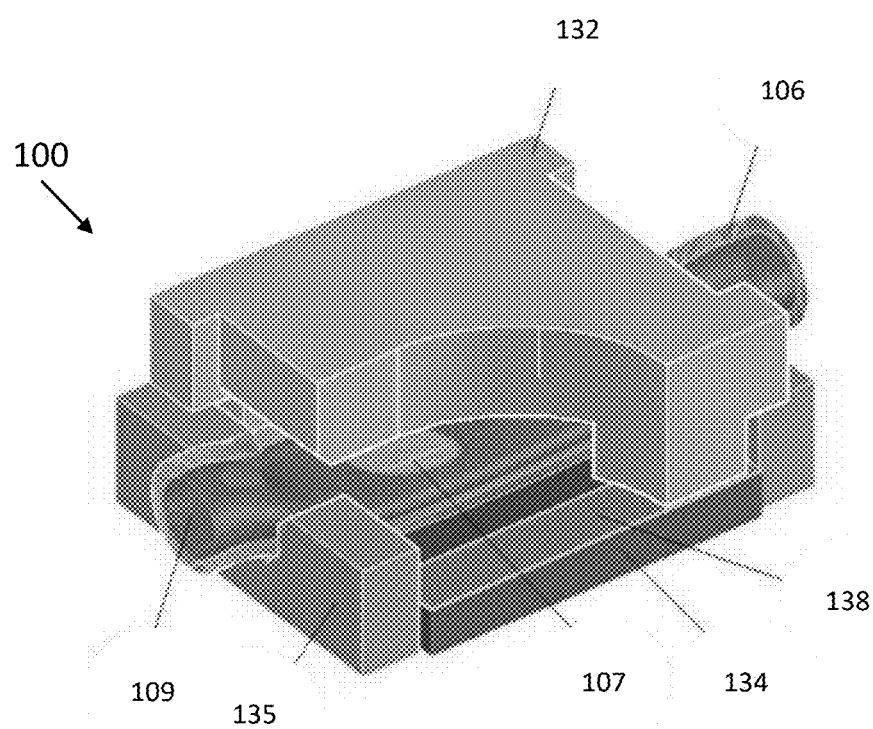
FIG. 3B depicts another example compartment of a pump, with a fluid delivery tube, in accordance with some example embodiments.

FIG. 2 illustrates a schematic diagram of the compartment 130 of the pump 122 and FIGS. 3A-3B illustrate an example compartment 130 of the pump 122, consistent with implementations of the current subject matter. The compartment 130 includes a door 132 and a base 134. The door 132 may be coupled (e.g., pivotably coupled) to the base 134, or another portion of the pump 122 that provides access to the base 134. For example, the door 132 may be opened (e.g., pivoted away from the base) or otherwise removed from the pump 122 to provide access to the base 134 and/or an interior volume 146 of the compartment 130. In some implementations, the door 132 is spring-loaded such that the door 132 is biased against the base 134 or another portion of the compartment 130 to help ensure that the door 132 remains closed in use. The interior volume 146 may be positioned between at least a portion of the base 134 and at least a portion of the door 132 when the door 132 is closed. In use, at least a portion of the fluid delivery tube 106 may be positioned within the interior volume 146 of the compartment 130 (see FIG. 3B).

The base 134 may include one or more (e.g., two) infusion set guides 135 (see FIGS. 3A and 3B). The infusion set guides 135 are positioned on opposite sides of the base 134. The infusion set guides 135 extend from the base 134 towards the interior volume 146. The infusion set guides 135 are spaced apart from one another and help to position the fluid delivery tube 106 within the interior volume 146. The infusion set guides 135 laterally fix and/or position the fluid delivery tube 106 within the compartment 130.

The base 134 may include one or more electrodes, such as one, two, three, or more electrodes. For example, the base 134 includes a first side electrode 136, a central electrode 137, and a second side electrode 138. The central electrode 137 is positioned between the first and second side electrodes 136, 138. The central electrode 137 is positioned such that the fluid delivery tube 106 is positioned along and/or in contact with the central electrode 137 and the fluid delivery tube 106 is not positioned along and/or in contact with the first and second side electrodes 136, 138. As such, the first and second side electrodes 136, 138 may be spaced apart from the central electrode 137 on opposing sides of the central electrode 137.

In some implementations, the first side electrode 136, the central electrode 137, and the second side electrode 138 may be integrally formed with the base 134 and/or may be separately coupled to the base 134. For example, the base 134 may include or form a substrate 139, such as a printed circuit board (PCB). The first side electrode 136, the central electrode 137, and the second side electrode 138 may be etched in the substrate 139, and may be exposed to the interior volume 146. Etching the electrodes in the substrate 139 may help to simplify manufacturing of the pump system 100 (e.g., the compartment 130), and may decrease costs of producing the pump system 100.

Referring to FIGS. 2-3B, the door 132 includes a first side portion 132A, a central portion 132B, and a second side portion 132C. The central portion 132B is positioned between the first and second side portions 132A, 132C. The first and second side portions 132A, 132C may be spaced apart from one another by the central portion 132B on opposing sides of the central portion 132B. The first side portion 132A, the central portion 132B, and the second side portion 132C may be integrally formed. The first side portion 132A and the second side portion 132C may each include a tab that extends inwardly towards the interior volume 146 by an amount that is greater than the central portion 132B. The tab of each of the first side portion 132A and the second side portion 132C may have a length that is the same as the length of each of the infusion set guides 135.

The first side portion 132A (e.g., the tab of the first side portion), the central portion 132B, and the second side portion 132C (e.g., the tab of the second side portion) may each include an interior surface, such as a first side surface 141A, a central surface 141B, and a second side surface 141C. The first side surface 141A, the central surface 141B, and the second side surface 141C may each face inwardly towards the interior volume 146 of the compartment 130.

In some implementations, the door 132 includes a conductive material, such as a metal. In some implementations, at least a portion of the door 132 includes the conductive material, such as at the first side surface 141A, the central surface 141B, and the second side surface 141C.

As noted above, the compartment 130 may be closed or opened (e.g., the door 132 may be closed and/or opened relative to the base 134). The door 132 may be closed relative to the base 134 of the compartment 130 when at least a portion of the door 132, such as the first side surface 141A, the central surface 141B, and the second side surface 141C, is approximately parallel to at least a portion of the base 134, such as the first side electrode 136, the central electrode 137, and the second side electrode 138.

When the compartment 130 is closed, at least a portion of the door 132 may be separated from at least a portion of the base 134 by a distance. For example, the first side surface 141A may be spaced apart from the first side electrode 136 by gap having a side distance 143, the central surface 141B may be spaced apart from the central electrode 137 by a gap having a central distance 148, and the second side surface 141C may be spaced apart from the second side electrode 138 by a gap having the side distance 143. In some implementations, the side distance 143 may be approximately 0.1 mm. In other implementations, the side distance 143 is approximately 0.05 mm to 0.1 mm, 0.1 mm to 0.3 mm, 0.3 mm to 0.5 mm, 0.5 mm to 1.0 mm, 1.0 mm to 1.5 mm, 1.5 mm to 2.0 mm, or greater. In some implementations, the central distance 148 may be approximately 30 times the size of the side distance 143. For example, in some implementations, the central distance 148 is approximately 3 mm, or approximately equal to a diameter of the fluid delivery tube 106. In other implementations, the central distance 148 is approximately 2.0 mm to 2.5 mm, 2.5 mm to 3.0 mm, 3.0 mm to 3.5 mm, 3.5 mm to 4.0 mm, or greater.

In some implementations, such as when the compartment 130 is closed, the compartment 130 forms a system of capacitors. For example, when the door 132 is closed relative to the base 134, the compartment forms a first side capacitor 140 (also referred to herein as "C1"), a central capacitor 142 (also referred to herein as "C2"), and a second side capacitor (also referred to herein as "C3"). The first side capacitor 140 may be defined by the first side electrode 136 and the first side portion 132A of the door (e.g., the tab of the first portion). The central capacitor 142 may be defined by the central electrode 137 and the central portion 132B of the door 132. In some implementations, the central capacitor 142 may also include the fluid delivery tube 106 when the fluid delivery tube 106 is positioned within the compartment 130. The second side capacitor 144 may be defined by the second side electrode 138 and the second side portion 132C of the door 132. In some implementations, power is supplied to each of the first side, central, and second side electrodes 136, 137, 138, which causes a potential difference between the first side, central, and second side electrodes 136, 137, 138 and the corresponding portions of the door 132A, 132B, 132C.

In some implementations, the controller 108 of the pump 122 measures a capacitance of the first side capacitor 140, the second side capacitor 144, and the central capacitor 142. The first side capacitor 140 and the second side capacitor 144 are coupled in series with one another, such that the capacitances measured from each of the first side capacitor 140 and the second side capacitor 144 are totaled. When no air is present within the portion of the fluid delivery tube 106 in the compartment 130, the total capacitance measured from the first side capacitor 140 and the second side capacitor 144 is approximately equal to the capacitance measured from the central capacitor 142.

In some implementations, the controller 108 of the pump 122 measures a value of capacitance of each of the first side capacitor 140, the second side capacitor 144, and the central capacitor 142 at various time increments, such as every second, minute, hour, and the like, and may compare the values at each time increment. As described herein, the capacitance may be measured simultaneously from the central capacitor 142 and the first and second side capacitors 140, 144. In some implementations, depending on the desired sensitivity and/or resolution of measurements (e.g., depending on the type of fluid), a running average of the measured values may be compared. For example, the running average of the measured capacitance values may be determined using the below equation, where t is the measurement time interval, C is the capacitance value, and a is a weight applied to each capacitance value or averaged capacitance value:

$$C_t = a*C_{t-1} + (1-a)*C_{measured}$$ Equation 1:

Generally, a capacitance may be a function of the amount of separation of two plates of the capacitor. In the example shown in FIGS. 2-3B, the two plates of the capacitors include each pairing of an electrode and corresponding portion of the door 132. In this example, the capacitance of the first and second side capacitors 140, 144 is a function of at least the side distance 143 and the capacitance of the central capacitor 142 is a function of at least the central distance 148. Thus, as the side distance 143 and/or the central distance 148 increases, the capacitance of each capacitor decreases. Alternatively, as the side distance 143 and/or the central distance 148 decreases, the capacitance of each capacitor increases.

When a dielectric material is inserted between the two plates of the capacitor (e.g., the fluid delivery tube 106 having the fluid 109), the capacitance of the capacitor in which the dielectric material is inserted, will change. For example, introducing a dielectric material having a dielectric constant greater than 1.0 will increase the capacitance of the capacitor. Air, which is positioned between the two plates of the first and second side capacitors 140, 144, has a dielectric constant approximately equal to 1.0, while the tube being fully filled with medication or other fluid generally has a dielectric constant approximately equal to 80.0. Thus, as described above, to compensate for the difference in dielectric constant of the dielectric material positioned within each of the first and second side capacitors 140, 144 and the central capacitor 142, the two plates of the first and second side capacitors 140, 144 are positioned in greater proximity with respect to one another than the two plates of the central capacitor 142. In other words, the first side portion 132A and first side electrode 136, and the second side portion 132C and second side electrode 138 are positioned closer to one another than the central portion 132B and the central electrode 137. This allows the total capacitance of the first and second side capacitors 140, 144 to be approximately equal to the capacitance of the central capacitor 142.

The multiple capacitors described herein provide for more reliable and/or accurate detection of air present within the fluid delivery tube 106. FIG. 3B shows an example of the compartment 130, in which a portion of the fluid delivery tube 106 is inserted within the compartment 130, and an air bubble 107 is positioned within the fluid 109 in the portion of the fluid delivery tube 106. Since the air bubble 107 has a lower dielectric constant than the surrounding fluid 109, the capacitance of the central capacitor 142, measured by the controller 108, will decrease or otherwise change. As the material (e.g., air) positioned in the first and second side capacitors 140, 144 does not change, the capacitance of the first and second side capacitors 140, 144 remains constant. Thus, the controller 108 may detect that the air bubble 107 is present within the portion of the fluid delivery tube 106 when the controller 108 detects a change, such as a decrease, in the capacitance of the central capacitor 142 and/or when the measured capacitance of the central capacitor 142 is not the same as the total capacitance of the first and second side capacitors 140, 144. The redundancy in sets of capacitances compared to one another helps to increase reliability of the pump system, such as in detecting air present within the fluid delivery tube 106. This may help to prevent or reduce the likelihood of an air embolism or other complications caused by air entering the patient's bloodstream. Additionally and/or alternatively, as external environmental changes occur, the capacitances measured at the first and second side capacitors 140, 144, and at the central capacitor 142, are impacted in the same way (e.g., by the same measurement error). Because the combination of capacitances of the first and second side capacitors 140, 144 is compared with the capacitance of the central capacitor 142, the error is cancelled out and/or otherwise balanced.

In a similar manner, the pump system 100 may determine whether a second fluid has been inserted into the portion of the fluid delivery tube 106, particularly when the second material has a dielectric constant that is different from the original fluid positioned within the portion of the fluid delivery tube 106. For example, since the second fluid has a different dielectric constant from the original fluid 109, the capacitance of the central capacitor 142, measured by the controller 108, will decrease, increase, or otherwise change. Thus, the controller 108 may detect that the second fluid is present within the portion of the fluid delivery tube 106 when the controller 108 detects a change, such as a decrease or increase, in the capacitance of the central capacitor 142 and/or when the measured capacitance of the central capacitor 142 is not the same as the total capacitance of the first and second side capacitors 140, 144. This example may be especially useful when multiple drug protocols are administered to a patient using the same pump 122 and/or tube 106.

Similarly, the pump system 100 may determine whether an infusion set, such as a tube 106 filled with fluid, is present within the compartment 130 of the pump 122. For example, since the fluid 109 within the fluid delivery tube 106 has a different dielectric constant than air (which would be positioned within the central capacitor 142 if no fluid 109 within the fluid delivery tube 106 is present), the capacitance of the central capacitor 142, measured by the controller 108, will increase, or otherwise change when the fluid 109 is introduced to the fluid delivery tube 106. Thus, the controller 108 may detect that the fluid 109 and/or tube 106 is present within the compartment 130 when the controller 108 detects a change, such as a decrease or increase, in the capacitance of the central capacitor 142 and/or when the measured capacitance of the central capacitor 142 is not the same as the total capacitance of the first and second side capacitors 140, 144. This configuration can help detect when there are any blockages or other occlusions in the fluid delivery tube 106 upstream of the compartment 130, for example.

In some implementations, the pump system 100 (e.g., the controller 108) may additionally and/or alternatively detect whether the door 132 of the compartment 130 is properly closed. For example, the controller 108 may measure the capacitance of the first and second side capacitors 140, 144. When the door 132 is closed, the capacitance of the first and second side capacitors 140, 144 may be relatively high (due at least in part to the small side distance 143), while when the door is opened, the capacitance of the first and second side capacitors 140, 144 may be relatively low (due at least in part to the greater side distance 143). In other words, the capacitance is in inverse proportion relative to the distance between the electrodes and corresponding portions of the door 132. Thus, the controller 108 may detect when the capacitance of the first and second side capacitors 140, 144 is within an acceptable range that indicates that the door 132 is opened and/or closed.

For example, when the door 132 is closed, the capacitance of the first and second side capacitors 140, 144 may be approximately 8 to 12 pico-farads, 10 to 14 pico-farads, or 12 to 16 pico-farads or greater. Thus, the pump system 100 (e.g., the controller 108) may detect that the door 132 is closed when the capacitance of the first and second side capacitors 140, 144 is approximately 8 to 12 pico-farads, 10 to 14 pico-farads, or 12 to 16 pico-farads or greater. When the door 132 is opened, the capacitance of the first and second side capacitors 140, 144 may be approximately 0.1 to 0.3 pico-farads, 0.2 to 0.4 pico-farads, or 0.3 to 0.5 pico-farads, and/or the like. Thus, the pump system 100 (e.g., the controller 108) may detect that the door 132 is opened when the capacitance of the first and second side capacitors 140, 144 is approximately 0.1 to 0.3 pico-farads, 0.2 to 0.4 pico-farads, or 0.3 to 0.5 pico-farads, and/or the like. Such configurations eliminates or reduces the need for an independent sensor (e.g., a magnetic, optical, or electromechanical sensor) for detecting when the door 132 of the compartment 130 is closed, thereby reducing the overall cost of the pump system.

Figure 4:
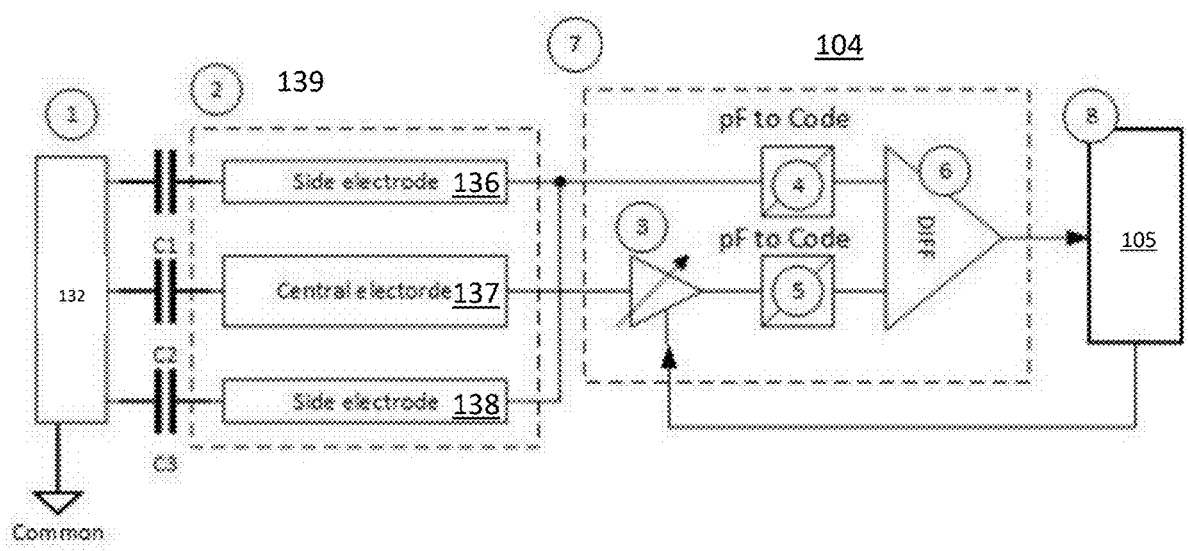
FIG. 4 depicts a schematic diagram representing a pump system, in accordance with some example embodiments.

FIG. 4 illustrates a schematic circuit diagram representing the pump system 100, consistent with implementations of the current subject matter. As shown in FIG. 4, the pump system 100 includes three capacitors (e.g., the first side capacitor 140, the central capacitor 142, and the second side capacitor 144). Each of the capacitors is formed by parallel plates. For example, the first side capacitor (C1) 140 is defined by the door 132 and the first side electrode 136, the second side capacitor (C3) 144 is defined by the door 132 and the second side electrode 138, and the central capacitor (C2) 142 is defined by the door 132 and the central electrode 137. The first side electrode 136, the central electrode 137, and the second side electrode 138 are positioned on and/or etched onto a substrate 139, such as a printed circuit board. As noted above, the first side electrode 136 and second side electrode 138 are connected in series.

The capacitance signal from the first side capacitor 140, the central capacitor 142, and the second side capacitor 144 is then processed by the processing circuitry 104. The processing circuitry includes an amplifier or other offset compensation component (3), a first capacitance-to-digital converter (e.g., a pF to Code converter) (4), a second capacitance-to-digital converter (e.g., a pF to Code converter) (5), and a differentiator (6). As shown in FIG. 4, the total capacitance signal from the first side capacitor 140 and second side capacitor 144 passes directly to the first capacitance-to-digital converter (4) and differentiator (6) to be converted to a digital signal. The capacitance signal from the central capacitor passes through the amplifier (3) before passing to the second capacitance-to-digital converter (5) and differentiator (6) to be converted to a digital signal. The capacitance signal from the central capacitor 142 passes to the amplifier (3) to ensure that the output of the total capacitance signal from the first side capacitor 140 and second side capacitor 144 is equal in value with the output of the capacitance signal from the central capacitor 142. The controller 108 may adjust the capacitance signal from the central capacitor 142 via amplifier (3), to compensate for one or more factors, such as environmental factors (e.g., temperature, humidity, air pressure, etc.), dielectric constants of materials positioned within the central capacitor, and/or the like, to balance the total capacitance measured from the first side capacitor 140 and second side capacitor 144 with the capacitance measured from the central capacitor 142. As a result, the pump system 100 described herein may reliably detect air within the fluid delivery tube 106, detect whether the infusion set is present in the pump 122, measure whether the door 132 of the pump 122 is properly closed during use, and/or detect when a different type of medication is injected into the infusion set, and/or the like, while negating the impact of any environmental changes during use of the pump 122.

Figure 5:
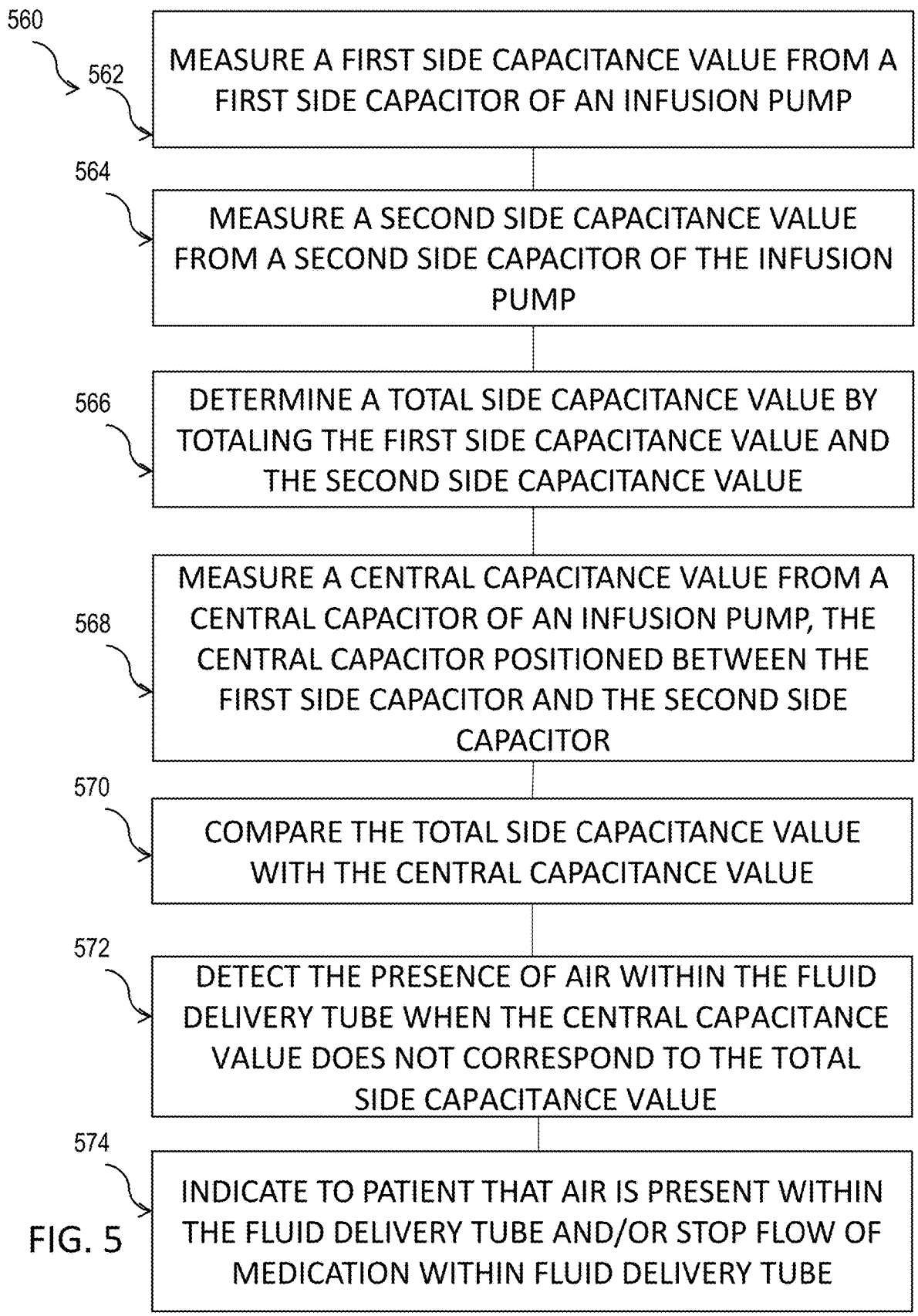
FIG. 5 depicts a flow diagram for detecting the presence of air in a fluid delivery tube of a pump, in accordance with some example embodiments.

FIG. 5 depicts a flowchart illustrating a process 560 for detecting the presence of air in a fluid delivery tube coupled with a pump for delivery of a medication to a patient.

At 562, a pump (e.g., the pump 122), such as via a controller (e.g., the controller 108), may measure and/or record a first side capacitance value from a first side capacitor (e.g., the first side capacitor 140) of an infusion pump (e.g. the pump 122) and at 564, the pump may measure a second side capacitance value from a second side capacitor (e.g., the second side capacitor 144) of the infusion pump. As noted above, the infusion pump may include a compartment (e.g., the compartment 130). The compartment may include a door (e.g., the door 132) and at least one electrode (e.g., the first side electrode 136, the second side electrode 138, and the central electrode 137) positioned within the compartment. The first side capacitor may be formed by at least a portion of the door, such as a first side portion (e.g., the first side portion 132A) and the first side electrode. The second side capacitor may be formed by at least another portion of the door, such as a second side portion (e.g., the second side portion 132C) and the second side electrode. In some implementations, the first side capacitance value and/or the second side capacitance value may be approximately 15 pF. In other implementations, the first side capacitance value and/or the second side capacitance value may be approximately 15 fF to 15 pF, 15 fF to 50 fF, 50 fF to 0.1 pF, 0.1 pF to 1.0 pF, 1.0 pF to 10 pF, or greater. The controller may detect a position of the door, fluid tubing, or other characteristic of the medical device. Upon detection, the controller may begin collecting the measurements. In some implementations, the frequency of measurement collection may be a statically configured value or may be performed based on a dynamically established frequency. The dynamic frequency may be determined based on a programming parameter for the pump (e.g., flow rate, medication to be administered), type of administration set inserted into the pump, or other characteristic detectable or accessible by the controller.

At 566, the pump may determine a total side capacitance value. For example, the pump, such as via the controller, may total the first side capacitance value and the second side capacitance value. In some implementations, the controller may total the first side capacitance value and the second side capacitance value at various time increments, such as every second, minute, hour, and the like. In some implementations, the controller records the total capacitance value. In some implementations, the total side capacitance value may indicate whether the door of the compartment of the pump is properly closed. For example, the pump may determine that the door is properly closed when the total side capacitance value is high, such as approximately 8 to 12 pico-farads, 10 to 14 pico-farads, or 12 to 16 pico-farads or greater. Alternatively, the pump may determine that the door is improperly closed, opened, or at least partially opened, when the total capacitance value is low, such as approximately 0.1 to 0.3 pico-farads, 0.2 to 0.4 pico-farads, or 0.3 to 0.5 pico-farads, and/or the like.

At 568, the pump, such as via a controller, may measure and/or record a central capacitance value from a central capacitor (e.g., the central capacitor 142) of the infusion pump. The central capacitor may be formed by at least a portion of the door, such as a central portion (e.g., the central portion 132B) and the central electrode within the compartment. In some implementations, the central capacitor may be formed by the central portion of the door, the central electrode, and a fluid delivery tube coupled to the pump for delivering a medication to a patient. The fluid delivery tube defines a dielectric material positioned between the central electrode and the central portion of the door. The central capacitor may be positioned between the first side capacitor and the second side capacitor. In some implementations, the central capacitance value may be approximately equal to the total capacitance value (e.g., the total of the first side capacitance value and the second side capacitance value). For example, the central capacitance value may be approximately 15 pF. In other implementations, the first side capacitance value and/or the second side capacitance value may be approximately 15 fF to 15 pF, 15 fF to 50 fF, 50 fF to 0.1 pF, 0.1 pF to 1.0 pF, 1.0 pF to 10 pF, or greater.

As described, the capacitance values may represent values detected at a specific time. In some implementations, the values may be generated based on an aggregation of several measurements. For example, a side capacitor value may be generated as a moving average based on a predetermined number of measurements collected by the corresponding side capacitor.

At 570, the pump, such as via the controller, may compare the total side capacitance value with the central capacitance value. In some implementations, no air is present within the fluid delivery tube when the total side capacitance value is approximately equal to, or with a range of (e.g., within 1%, 2%, 3%, 4%, or 5%), the measured central capacitance value. Similarly, the pump (e.g., via the controller) may determine that an infusion set (e.g., a fluid delivery tube filled with medication) is present within the compartment of the pump when the central capacitance value and the total side capacitance value are approximately equal or within a range of one another. In some implementations, air may be present within the fluid delivery tube when the total side capacitance value is greater than, or outside of a range of (e.g., greater than 1%, 2%, 3%, 4%, or 5%), the measured central capacitance value. The range may be a parameter programmed to the pump by a user via a user interface, the range may be a static value configured for the pump, or the range may be a dynamic value generated based on one or more values detectable or accessible by the pump.

At 572, the pump may detect the presence of air within the fluid delivery tube when the central capacitance value does not correspond to (e.g., differs by at least a threshold amount) the total side capacitance value. As noted above, in some implementations, the pump may detect the presence of air within the fluid delivery tube when the total side capacitance value is greater than, or outside of a range of, the measured central capacitance value.

At 574, based on the determination that air is present within the fluid delivery tube, the pump may adjust one or more operational element associated with the fluid delivery. For example, the pump may adjust a user interface, light, or audio component to present a human-perceivable indication that air is present within the fluid delivery tube. As another example, the pump may disable a pumping mechanism or engage an occluder to stop flow of medication to the patient from within the fluid delivery tube. In some implementations, the pump may communicate with a local or wireless accessory system (e.g., the accessory system 102), such as via a display of the pump or separate client device to indicate that air is present within the fluid delivery tube (e.g., an amount of air that is greater than a threshold amount) and/or that the pump is preventing flow of medication to the patient. For example, the pump may display an indicator, such as an alarm, text, flashing lights, and/or the like.

Figure 6:
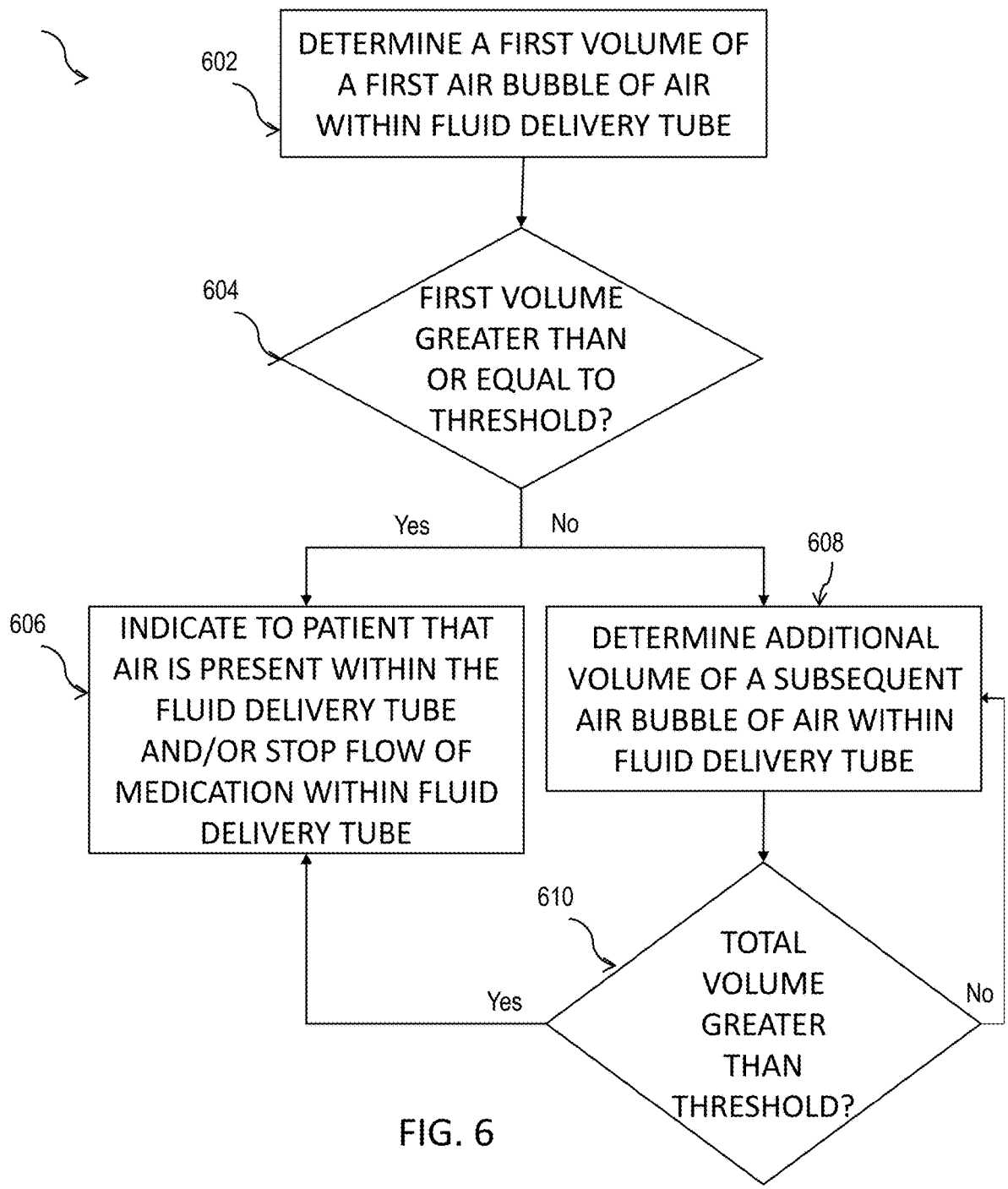
FIG. 6 depicts a flow diagram for detecting the presence of an unacceptable amount of air in a fluid delivery tube of a pump, in accordance with some example embodiments.

FIG. 6 illustrates a process flow diagram 600 for detecting the presence of an amount of air that is greater than a threshold amount of air within fluid delivery tube coupled with a pump for delivery of a medication to a patient.

At 602, the pump, such as via a controller, may, using one or more of the methods described herein, detect the presence of air within the fluid delivery tube. The air within the fluid delivery tube may include one or more air bubbles, such as a first air bubble, a second air bubble, and so on. In some implementations, based on at least the central capacitance value measured from the central capacitor, the pump may determine a first volume of the first air bubble of the air within the fluid delivery tube. For example, the pump may measure and determine a total capacitance of the first and second side capacitors, when a door of the pump is closed. The pump may assume that the capacitance of the central capacitor is approximately equal to the total capacitance of the first and second side capacitors when the fluid delivery tube is fully filled with fluid. Once the fluid delivery tube is inserted into the pump, the pump measures and records a maximum value of the central capacitance of the central capacitor over a period of time. The maximum value of the central capacitance may be stored as the central capacitance value when the fluid delivery tube is fully filled with fluid. Accordingly, the capacitance values (e.g., the central capacitance and/or the total capacitance of the side capacitors) measured and/or determined during infusion of the fluid may indicate a proportional air presence compared to a known total volume of fluid within the fluid delivery tube. For example, the change in the central capacitance value may be proportional to the change in volume of fluid within the fluid delivery tube. The decrease in volume of fluid within the fluid delivery tube when air is present within the fluid delivery tube corresponds to the volume (e.g., the first volume) of each air bubble of the air within the fluid delivery tube. In some implementations, the first volume of the first air bubble may be approximately 1 ml. In other implementations, the first volume of the first air bubble may be approximately 0.01 ml to 0.05 ml, 0.05 ml to 0.10 ml, 0.10 ml to 0.50 ml, or 0.50 ml to 1 ml, or greater.

At 604, the pump, such as via the controller, may determine whether the first volume of the first air bubble is greater than a threshold volume. In some implementations, the threshold volume is approximately 1 ml. In other implementations, the threshold volume may be approximately 0.01 ml to 0.05 ml, 0.05 ml to 0.10 ml, 0.10 ml to 0.50 ml, or 0.50 ml to 1 ml, or greater. The threshold volume may be equivalent to an acceptable amount of air to pass through the fluid delivery tube without causing an air embolism, or other complications due to the air passing into the patient's bloodstream. The threshold may be a parameter programmed to the pump by a user via a user interface, a parameter included in patient information received by the pump, a static value configured for the pump, or a dynamic value generated based on one or more values detectable or accessible by the pump.

If the pump determines that the first volume of the first air bubble corresponds to (e.g., is greater than or equal to) the threshold volume, at 606, the pump may adjust one or more operational element associated with the fluid delivery. For example, the pump may adjust a user interface, light, or audio component to present a human-perceivable indication that air is present within the fluid delivery tube. As another example, the pump may disable a pumping mechanism or engage an occluder to stop flow of medication to the patient from within the fluid delivery tube. In some implementations, the pump may communicate with a local or wireless accessory system, such as via a display of the pump or separate client device to indicate to the patient that the unacceptable amount of air is present within the fluid delivery tube (e.g., a volume of air that is greater than the threshold volume) and/or that the pump is preventing flow of medication to the patient. For example, the pump may display an indicator, such as an alarm, text, flashing lights, and/or the like.

If the pump determines that the first volume of the first air bubble is less than the threshold volume, the pump may store the first volume of the first air bubble at the initial value for a total air volume. The pump, such as via a controller, may, using one or more of the methods described herein, detect the presence of another air bubble of the air within the fluid delivery tube. In some implementations, at 608, based on at least the central capacitance value measured from the central capacitor, the pump may determine an additional volume of a subsequent air bubble (e.g., subsequent to the air bubbles previously detected by the method) of the air within the fluid delivery tube. The additional volume of the subsequent air bubble may be determined in the same or similar manner as the first volume of the first air bubble. In some implementations, the additional volume of the subsequent air bubble may be approximately 1 ml. In other implementations, the volume of the subsequence air bubble may be approximately 0.01 ml to 0.05 ml, 0.05 ml to 0.10 ml, 0.10 ml to 0.50 ml, or 0.50 ml to 1 ml, or greater.

The pump, such as via the controller, may combine a current total air volume and the additional volume of the subsequent air bubble to generate a new value for the total air volume. At 610, the pump, such as via the controller, may determine whether the total air volume is greater than or equal to the threshold volume. If the pump determines that the total volume is less than the threshold volume, the pump stores the new total volume, and returns to 608 to continue to monitoring the fluid within the fluid delivery tube for additional air bubbles.

If the pump determines that the total volume of the air bubbles (e.g., the total volume of the first air bubble and any accumulated subsequent bubble volumes) exceeds the threshold, the method may proceed to 606, as described above. Thus, the pump may reliably and accurately detect the presence of air, such as an unacceptable amount of air, within the fluid delivery tube. This can help prevent or reduce the likelihood of an air embolism or other medical complications for the patient.

Figure 7:
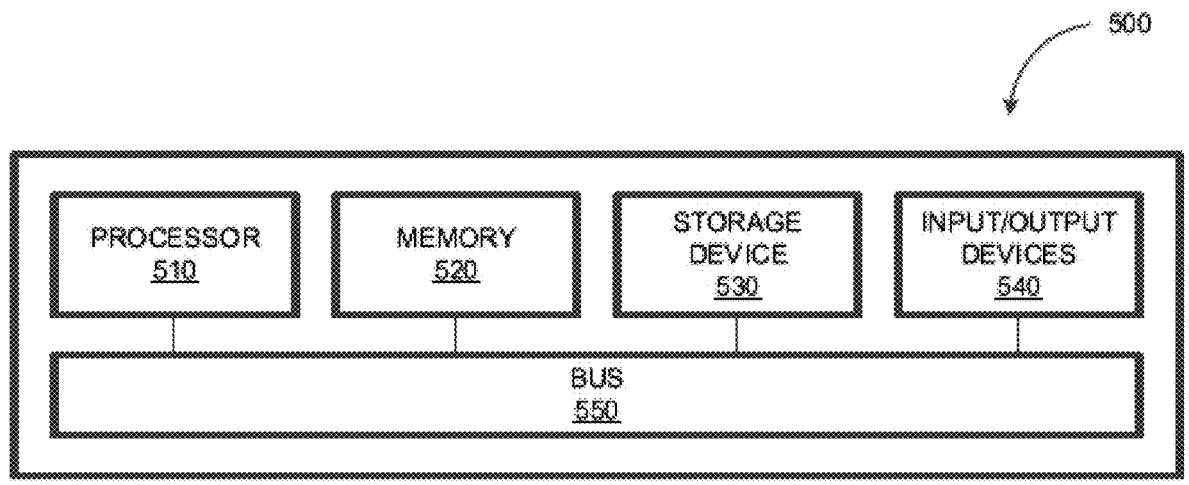
FIG. 7 depicts a block diagram illustrating a computing system, in accordance with some example embodiments.

FIG. 7 depicts a block diagram illustrating a computing system 500 consistent with implementations of the current subject matter. Referring to FIGS. 1 and 7, the computing system 500 can be used to implement the pump 122, the accessory system 102, the display 154, and/or any components therein.

As shown in FIG. 7, the computing system 500 can include a processor 510, a memory 520, a storage device 530, and input/output devices 540. The processor 510, the memory 520, the storage device 530, and the input/output devices 540 can be interconnected via a system bus 550. The processor 510 is capable of processing instructions for execution within the computing system 500. Such executed instructions can implement one or more components of, for example, the pump 122. In some example embodiments, the processor 510 can be a single-threaded processor. Alternatively, the processor 510 can be a multi-threaded processor. The processor 510 is capable of processing instructions stored in the memory 520 and/or on the storage device 530 to present graphical information for a user interface provided via the input/output device 540.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a floppy disk device, a hard disk device, an optical disk device, or a tape device, or other suitable persistent storage means. The input/output device 540 provides input/output operations for the computing system 500. In some example embodiments, the input/output device 540 includes a keyboard and/or pointing device. In various implementations, the input/output device 540 includes a display unit for displaying graphical user interfaces.

According to some example embodiments, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some example embodiments, the computing system 500 can be used to execute various interactive computer software applications that can be used for organization, analysis and/or storage of data in various formats. Alternatively, the computing system 500 can be used to execute software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 540. The user interface can be generated and presented to a user by the computing system 500 (e.g., on a computer screen monitor, etc.).

Figure 8A:
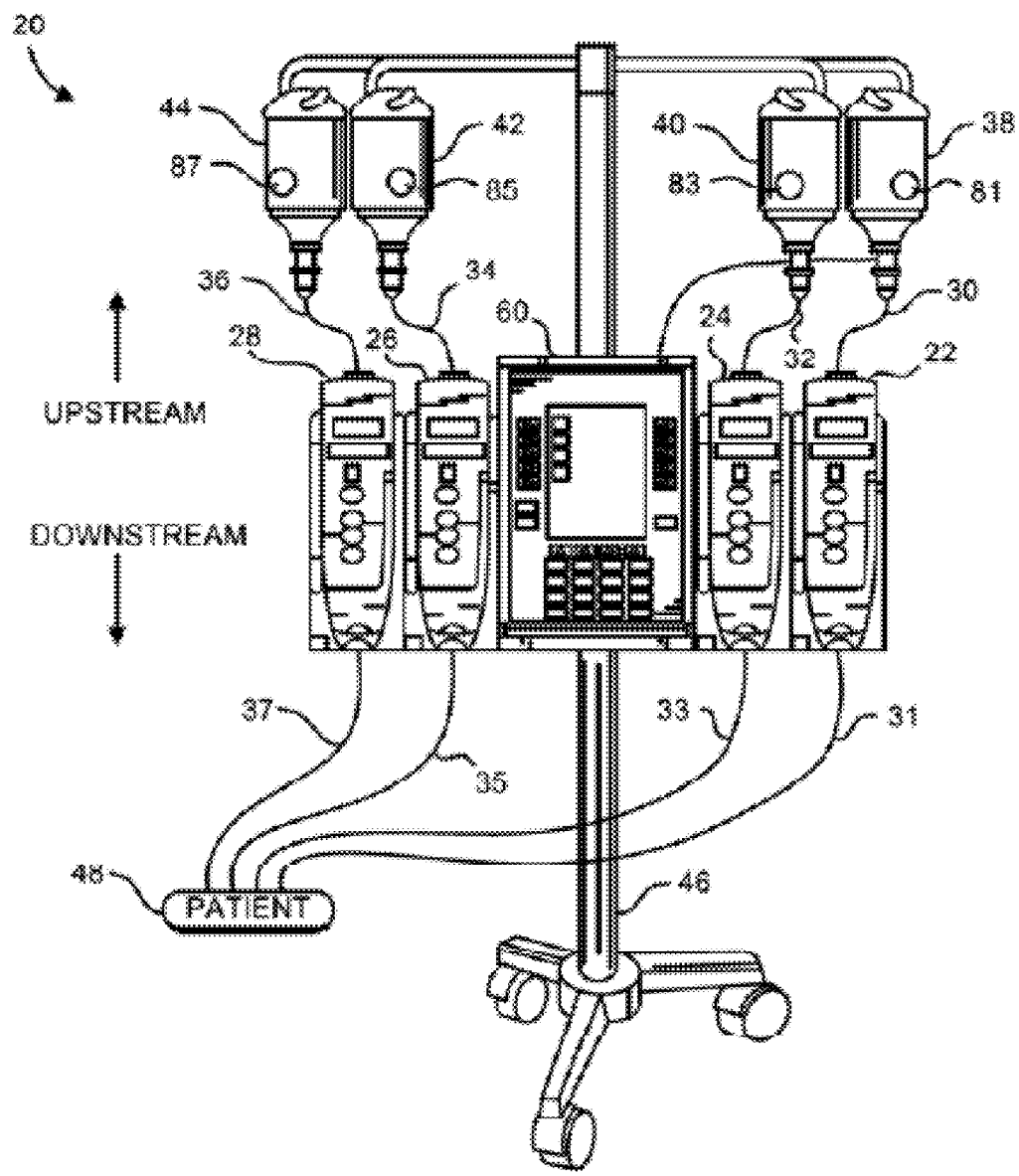
FIG. 8A depicts a front view of a patient care system, in accordance with some example embodiments.
Figure 8B:
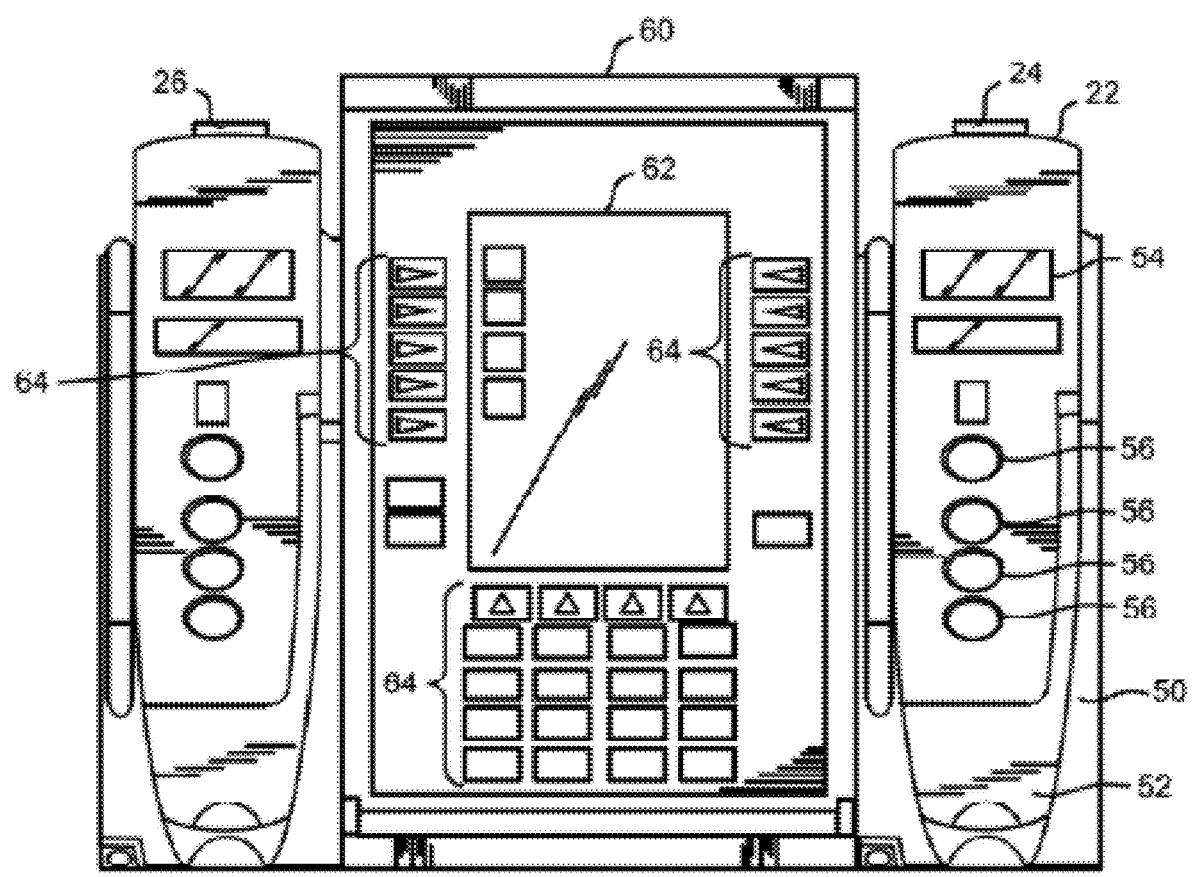
FIG. 8B depicts an enlarged view of a portion of a patient care system, in accordance with some example embodiments.
Figure 8C:
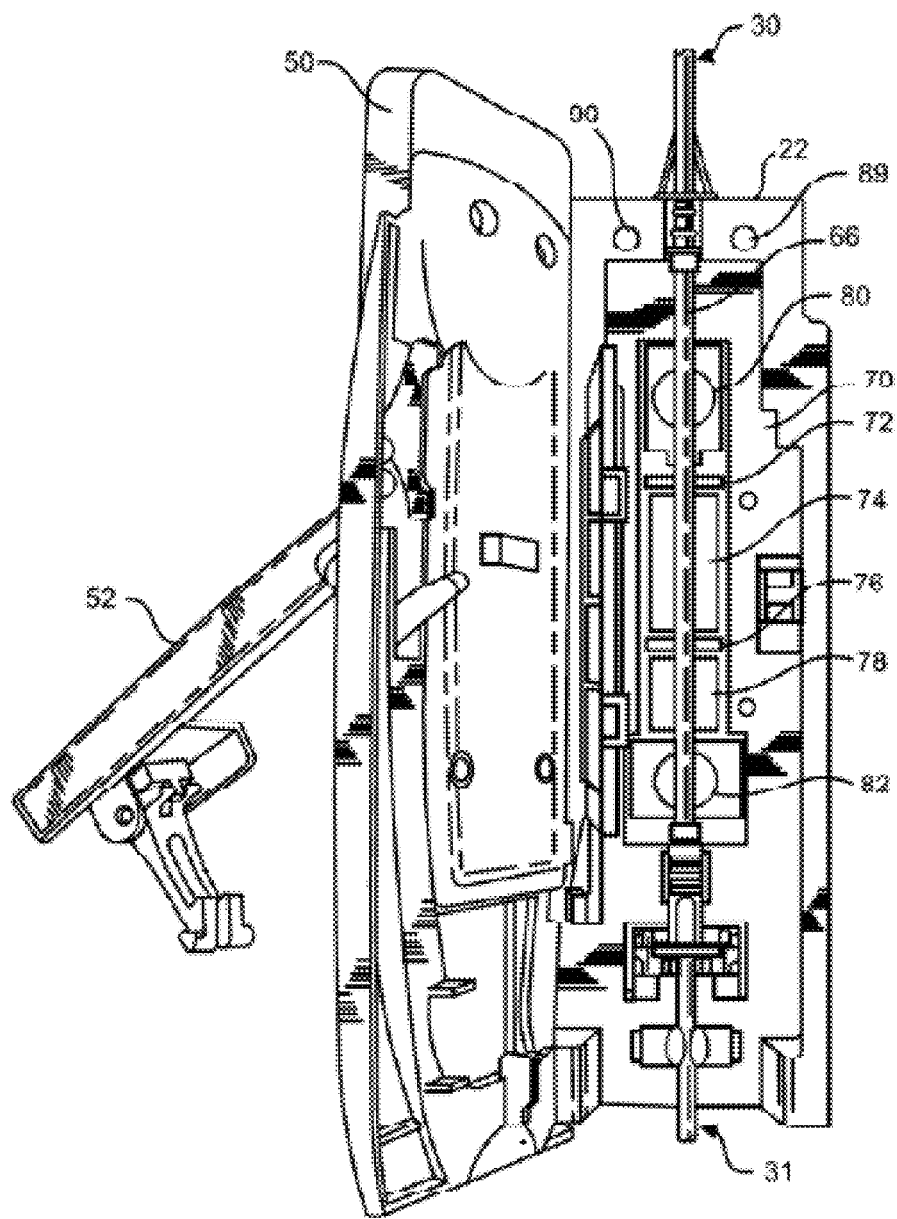
FIG. 8C depicts a perspective view of a pump, in accordance with some example embodiments.

In some example embodiments, the pump 122 (e.g., pump 22 as shown in FIGS. 8A-8C) may be part of a patient care system 20. FIGS. 8A-8C illustrate example embodiments of the patient care system 20, though other types of patient care systems may be implemented. Referring to FIG. 8A, the patient care system 20 may include the pump 22 as well as additional pumps 24, 26, and 28. Although a large volume pump (LVP) is illustrated, other types of pumps may be implemented, such as a small volume pump (SVP), a syringe pump, an anesthesia delivery pump, and/or a patient-controlled analgesic (PCA) pump configured to deliver a medication to a patient. The pump 22 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like, or the pump 22 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like. In some implementations, one or more of the pumps 22, 24, 26, 28 may include the compartment 130 as described herein.

As shown in FIG. 8A, each of the pump 22, 24, 26, and 28 may be fluidly connected with an upstream fluid line 30, 32, 34, and 36, respectively. Moreover, each of the four pumps 22, 24, 26, and 28 may also fluidly connected with a downstream fluid line 31, 33, 35, and 37, respectively. The fluid lines can be any type of fluid conduit, such as fluid delivery tube (e.g., the fluid delivery tube 106), through which fluid can flow. At least a portion of one or more of the fluid lines may be constructed with a multi-layered configuration as described herein. In some implementations, each of the pumps 22, 24, 26, and 28 may use the same fluid line. In such implementations, as described above, the pump system may detect when various types of fluid flow through the fluid line.

Fluid supplies 38, 40, 42, and 44, which may take various forms but in this case are shown as bottles, are inverted and suspended above the pumps. Fluid supplies may also take the form of bags, syringes, or other types of containers. Both the patient care system 20 and the fluid supplies 38, 40, 42, and 44 may be mounted to a roller stand or intravenous (IV) pole 46.

A separate pump 22, 24, 26, and 28 may be used to infuse each of the fluids of the fluid supplies into the patient. The pumps 22, 24, 26, and 28 may be flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other fluids.

Typically, medical fluid administration sets have more parts than are shown in FIG. 8A. Many have check valves, drip chambers, valved ports, connectors, and other devices well known to those skilled in the art. These other devices have not been included in the drawings so as to preserve clarity of illustration. In addition, it should be noted that the drawing of FIG. 8A is not to scale and that distances have been compressed for the purpose of clarity. In an actual setting, the distance between the bottles 38, 40, 42, and 44 and the pumps 22, 24, 26, and 28 could be much greater.

Referring now to FIG. 8B, an enlarged view of the front of the patient care system 20 is shown. The pump 22 may include a front door 50 (e.g., the door 132) and a handle 52 that operates to lock the door in a closed position for operation and to unlock and open the door for access to the internal pumping and sensing mechanisms and to load administration sets for the pump. The door may provide access to a compartment of the pump, such as the compartment 130. When the door is open, the tube (e.g., the fluid delivery tube 106) can be connected with the pump, as will be shown in FIG. 8C. When the door is closed, the tube is brought into operating engagement with the pumping mechanism, the upstream and downstream pressure sensors, and the other equipment of the pump. In some implementations, when the door is closed, the door may form at least one (e.g., three) capacitors with a base of the compartment. The capacitors may be used to detect the presence of air in the fluid lines, as described herein. A display 54 (e.g., the display 154), such as an LED display, is located in plain view on the door in this embodiment and may be used to visually communicate various information relevant to the pump, such as alert indications (e.g., alarm messages). The display 54 may otherwise be a part of or be coupled to the pump 22. Control keys 56 exist for programming and controlling operations of the pump as desired. The pump 22 also includes audio alarm equipment in the form of a speaker (not shown).

In the embodiment shown, a programming module 60 is attached to the left side of the pump 22. In some embodiments, the programming module 60 forms a part of the pump 22. Other devices or modules, including another pump, may be attached to the right side of the pump 22, as shown in FIG. 8A. In such a system, each attached pump represents a pump channel of the overall patient care system 20. In one embodiment, the programming module is used to provide an interface between the pump 22 and external devices as well as to provide most of the operator interface for the pump 22.

The programming module 60 includes a display 62 for visually communicating various information, such as the operating parameters of the pump 22 and alert indications and alarm messages. The programming module 60 may additionally and/or alternatively communicate with the accessory system 102 to, for example, indicate to the patient that the presence of air has been detected in at least one of the fluid lines. The programming module 60 may additionally and/or alternatively display on the display 54, an indication to the patient that the presence of air has been detected in at least one of the fluid lines. The programming module 60 may also include a speaker to provide audible alarms, such as when the presence of air has been detected in at least one of the fluid lines. The programming module or any other module also has various input devices in this embodiment, including control keys 64 and a bar code or other scanner or reader for scanning information from an electronic data tag relating to the infusion, the patient, the care giver, or other. The programming module also has a communications system (not shown) with which it may communicate with external equipment such as a medical facility server or other computer and with a portable processor, such as a handheld portable digital assistant ("PDA), or a laptop-type of computer, or other information device that a care giver may have to transfer information as well as to download drug libraries to a programming module or pump.

The communications system may take the form of a radio frequency ("RF") (radio frequency) system, an optical system such as infrared, a Bluetooth system, or other wired or wireless system. The bar code scanner and communications system may alternatively be included integrally with the pump 22, such as in cases where a programming module is not used, or in addition to one with the programming module. Further, information input devices need not be hard-wired to medical instruments, information may be transferred through a wireless connection as well.

FIG. 8B includes a second pump 26 connected to the programming module 60. As shown in FIG. 8A, more pump modules may be connected. Additionally, other types of modules may be connected to the pump modules or to the programming module.

Turning now to FIG. 8C, the pump 22 is shown in perspective view with the front door 50 open, showing the upstream fluid line 30 and downstream fluid line 31 in operative engagement with the pump 22. The pump 22 directly acts on a tube 66 (also referred to as a pump segment) that connects the upstream fluid line 30 to the downstream fluid line 31 to form a continuous fluid conduit, extending from the respective fluid supply 38 (FIG. 8A) to the patient 48, through which fluid is acted upon by the pump to move fluid downstream to the patient. Specifically, a pumping mechanism 70 acts as the flow control device of the pump to move fluid though the conduit. The upstream and downstream fluid lines and/or tube 66 may be coupled to a pump cassette or cartridge that is configured to be coupled to the pump 22, such as the type described in co-pending U.S. patent application Ser. No. 13/827,775, which is incorporated by reference herein.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the fluid delivery tube until the next one in sequence has already occluded the fluid delivery tube; thus at no time is there a direct fluid path from the fluid supply to the patient. The operation of peristaltic pumps including four finger pumps is well known to those skilled in the art and no further operational details are provided here.

In this particular embodiment, FIG. 8C further shows a downstream pressure sensor 82 included in the pump 22 at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 8A) and the flow control device, so that the connection of the correct fluid supply with the correct pump may be verified before any fluid is pumped to the patient.

With reference still to FIG. 8C, an upstream pressure sensor 80 may also be included in the pump 22. The upstream pressure sensor is assigned to the flow control device or pumping mechanism 70 and, in this embodiment, is further provided as an integral part of the pump 22. It is mounted to the flow control device 70 and is located adjacent and upstream in relation to the flow control device. The upstream pressure sensor is located upstream from the flow control device, that is, at a location between the fluid supply 38 (FIG. 8A) and the flow control device, so that the connection of the correct fluid supply with the correct pump may be verified before any fluid is pumped to the patient. In an implementation where the source is a syringe, the flow control device 70 may be configured to press a plunger of the syringe to provide the infusion according to the programmed parameters.

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An infusion pump system for detecting a presence of air within a fluid delivery tube coupled to an infusion pump for delivery of a medication to a patient, the infusion pump system comprising:
   a door comprising:
      a first side portion;
      a second side portion; and
      a central portion positioned between the first side portion and the second side portion;
   a base comprising:
      a first side electrode;
      a second side electrode; and
      a central electrode positioned between the first side electrode and the second side electrode,
   the fluid delivery tube, wherein the fluid delivery tube is positioned between the central electrode and the central portion of the door;
   a capacitor system comprising:
      a first side capacitor formed by the first side electrode and the first side portion;
      a second side capacitor formed by the second side electrode and the second side portion; and
      a central capacitor formed by the central portion, the fluid delivery tube, and the central electrode,
      wherein the presence of air within the fluid delivery tube is detected when a total side capacitance value is different from a central capacitance value of the central capacitor, the total side capacitance value being a total of a first side capacitance value of the first side capacitor and a second side capacitance value of the second side capacitor; and
   a controller, the controller comprising at least one data processor and at least one memory storing instructions, which when executed by the at least one data processor, result in operations comprising:
      measuring the first side capacitance value from the first side capacitor;
      measuring the second side capacitance value from the second side capacitor;
      determining the total side capacitance value by totaling the first side capacitance value and the second side capacitance;
      measuring the central capacitance value from the central capacitor; and
      comparing the total side capacitance value to the central capacitance value.

2. The infusion pump system of claim 1, wherein the presence of air within the fluid delivery tube is detected when the central capacitance value is less than the total side capacitance value.

3. The infusion pump system of claim 1, wherein the door comprises a metallic material.

4. The infusion pump system of claim 1, wherein the base comprises a substrate, and wherein the first side electrode, the second side electrode, and the central electrode are etched into the substrate.

5. The infusion pump system of claim 4, wherein the substrate is a printed circuit board.

6. The infusion pump system of claim 1, wherein the door is parallel to the base.

7. The infusion pump system of claim 1, wherein a side distance between the first side electrode and the first side portion of the door is less than a central distance between the central electrode and the central portion of the door.

8. The infusion pump system of claim 1, further comprising:
   the infusion pump.

9. The infusion pump system of claim 1, wherein the operations further comprise:
   determining that the central capacitance value is less than the total side capacitance value; and
   detecting, based on the determination that the total side capacitance value is less than the central capacitance value, the presence of air within the fluid delivery tube.

10. The infusion pump system of claim 9, wherein the operations further comprise:
    indicating to the patient that air is present within the fluid delivery tube, the indicating comprising one or more of playing a sound and a light.

11. The infusion pump system of claim 9, wherein the operations further comprise:
    stopping a flow of the medication within the fluid delivery tube upon the detecting of the presence of air within the fluid delivery tube.

12. The infusion pump system of claim 9, wherein the operations further comprise:
    determining, based on the central capacitance value, a volume of the air within the fluid delivery tube.

13. The infusion pump system of claim 12, wherein the operations further comprise; determining that the volume of the air is greater than a threshold volume of air; and indicating to the patient that air is present within the fluid delivery tube and/or stopping a flow of the medication within the fluid delivery tube upon the determining that the volume of the air is greater than the threshold volume.

14. The infusion pump system of claim 9, wherein the operations further comprise:
    determining, based on the central capacitance value, a volume of a first air bubble of the air within the fluid delivery tube.

15. The infusion pump system of claim 14, wherein the operations further comprise:
    determining that the volume of the first air bubble is greater than or equal to a threshold volume of air; and indicating to the patient that air is present within the fluid delivery tube and/or stopping flow of the medication within the fluid delivery tube upon determining that the volume of the first air bubble is greater than or equal to a threshold volume of air.

16. The infusion pump system of claim 14, wherein the operations further comprise:
    determining that the volume of the first air bubble is less than a threshold volume of air;
    determining a second volume of a second air bubble of the air within the fluid delivery tube based on a second central capacitance value;
    determining a total volume of air within the fluid delivery tube by totaling the volume of the first air bubble and the second volume of the second air bubble; and
    indicating to the patient that air is present within the fluid delivery tube and/or stopping flow of the medication within the fluid delivery tube upon determining that the total volume of volume of the first air bubble and the second volume of the second air bubble is greater than or equal to a threshold volume of air.

* * * * *